(12) United States Patent
Healy

(10) Patent No.: US 6,447,805 B1
(45) Date of Patent: Sep. 10, 2002

(54) IMPLANTATION COMPOSITION COMPRISING GLASS PARTICLES

(75) Inventor: David Michael Healy, Ayr (GB)

(73) Assignee: Giltech Limited, Ayr (GB)

( * ) Notice: Subject to any disclaimer, the term of this patent is extended or adjusted under 35 U.S.C. 154(b) by 0 days.

(21) Appl. No.: 09/402,506
(22) PCT Filed: Apr. 6, 1998
(86) PCT No.: PCT/GB98/01017
  § 371 (c)(1),
  (2), (4) Date: Feb. 15, 2000
(87) PCT Pub. No.: WO98/44965
  PCT Pub. Date: Oct. 15, 1998

(30) Foreign Application Priority Data

Apr. 5, 1997 (GB) .............................................. 9706967
Jun. 14, 1997 (GB) .............................................. 9712399

(51) Int. Cl.⁷ .................................................. A61K 9/14
(52) U.S. Cl. ..................................................... 424/489
(58) Field of Search ........................................ 424/489

(56) References Cited

U.S. PATENT DOCUMENTS 5,039,326 A * 8/1991 Day et al. ..................... 65/21.1
5,204,382 A    4/1993 Wallace

FOREIGN PATENT DOCUMENTS

| WO | WO 90 08470 | 8/1990 |
| WO | WO 91 17777 | 11/1991 |
| WO | WO 93 15721 | 8/1993 |
| WO | WO 93 16658 | 9/1993 |
| WO | WO 96 24364 | 8/1996 |
| WO | WO 97 33632 | 9/1997 |

* cited by examiner

Primary Examiner—Jose' G. Dees
Assistant Examiner—Konata M George
(74) Attorney, Agent, or Firm—Charles N. Quinn, Esq.; Fox, Rothschild, O'Brien & Frankel, LLP

(57) ABSTRACT

A composition suitable for implantation in soft tissue (for example at or around a body orifice) in order to augment the volume of soft tissue is produced. The particles, which are desirably irregularly shaped, are formed from a biodegradable phosphate glass, and may have an average particle diameter of 50 μm to 2000 μm, preferably 50 μm to 300 μm. The particles are used with a carrier medium for injection into soft tissue such as the bladder submucosa. This procedure can be applied to treat conditions such as vesicoureteric reflux. Additionally the procedure could be used cosmetically.

16 Claims, 3 Drawing Sheets

IMPLANTATION COMPOSITION COMPRISING GLASS PARTICLES

Figure 1:
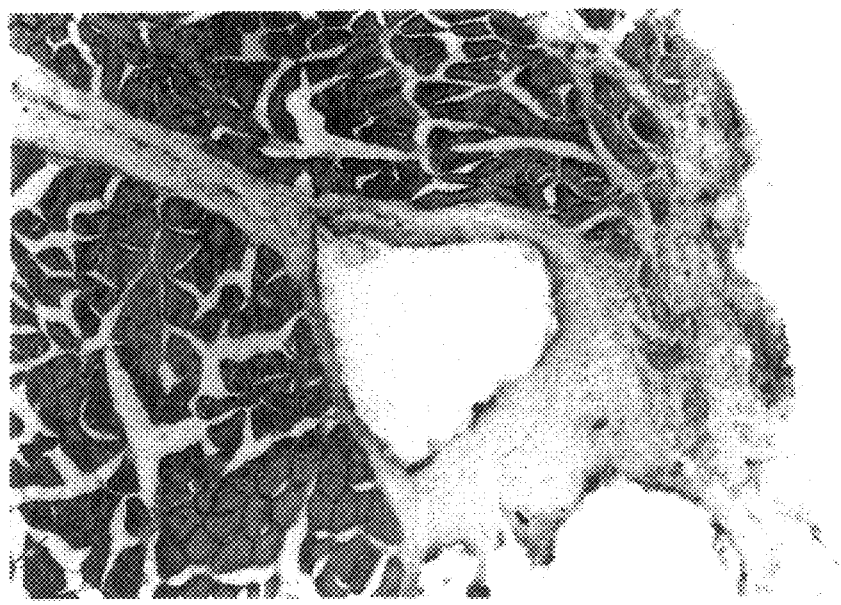

The present invention is concerned with a composition suitable for implantation at or in the vicinity of a body orifice or sphincter muscle to aid correct function.

Many body unctions rely upon the correct functioning of sphincter muscles. For example, the pyloric sphincter controls when the contents of the stomach pass into the small intestine. Similarly, the urethral sphincter controls when the contents of the bladder are voided. Incorrect functioning due to premature relaxation of such sphincter muscles can be problematic, and in the case of stress urinary incontinence (malfunction of the urethral sphincter) highly distressing to the patient.

Premature relaxation of a sphincter muscle often occurs when the Sphincter muscle itself lacks sufficient bulk to adequately close the orifice in question. One option to overcome the problem is by implanting bulking material in the submucosa surrounding the orifice, thereby reducing the area to be closed by the sphincter muscle. Generally, the bulking material is injected into the site to augment the soft tissue present. Suitable bulking materials are available commercially and are generally in the form of spherical particles or beads based on silicone, PTFE or collagen. These beads are suspended in a carrier fluid such as glycerine or hydrogel. The carrier fluid ants as a lubricant during the implantation process and assists expulsion of the implant from the syringe through an endoscopic needle. The carrier fluid is eliminated from the body and the implant material gradually becomes encapsulated by collagen at the implant site. The collagen capsule which forms around the implanted material adds to the bulk at the site. One such bulking material is MACROPLASTIQUE (Trade Mark) of Uroplasty, Inc.

Existing implants do not biodegrade but remain permanently in the body of the patient. Recently, concern has been raised that such implants may gradually migrate away form the site of implantation during the lifetime of the patient. Thus, the original problem may recur as the size of the implant gradually decreases due to migration of the beads inserted. The patient will therefore need to undergo a further procedure in order to insert more beads at the site concerned The migrating implant may, in addition, cause irritation and such implants have been reported to be associated with cancer, auto-immune and connective tissue disease.

In addition to stress urinary incontinence, such implants have also been used to prevent vesicoureteral reflux. Vesicoureteric reflux is a condition occurring in babies and small children where the ureteral orifice is incompletely closed during contraction of the bladder. Urine is thus allowed to reflux back up the ureter and can cause recurrent infections of the kidneys, frequently leading to permanent kidney damage. In a similar manner to stress urinary incontinence, it is possible to insert pellets or beads of silicone rubber or teflon in the submucosa of the bladder wall close to the ureteral orifice. Again, the procedure requires the permanent insertion of the implant.

Paediatric vesicoureteral reflux usually resolves itself as the bladder wall thickens. By the time a child is five years old the urinary system has usually matured sufficiently to make the implant material redundant. Again, it is possible for implant material to migrate from the implant site causing obstruction, occlusion or embolism at another site. Implants have also been associated with cancer, auto-immune and connective issue disease.

The present invention provides a composition suitable for implantation in soft tissue (for example at or around a body orifice) in order to augment the volume of soft tissue. The composition of the present invention comprises particles of biodegradable glass in a suitable carrier medium. The carrier medium is required to ensure easy injection at the site of interest.

The currently available silicone, PTFE and collagen beads are all deformable. This property aids injection of the beads, butalso contributes to their ability to migrate from the site of interest. By contrast, the glass particles of the present invention are non-deformable.

The composition is suitable for insertion in the bladder submucosa to treat stress urinary incontinence or vesioureteric reflux by bulking up the area around the urethral sphincter or urethral orifice respectively.

Optionally, the glass particles dissolve over a relatively long period, typically one to five years, more usually one to two years.

Preferably, the glass particles are irregularly shaped. This contrasts to the commercially available implants which are formed from spherically shaped beads. The irregular shape of the glass particles encourages their encapsulation in fibrous tissue. Such encapsulation further reduces the rate of dissolution of the glass and also helps to prevent migration of the particles.

Typically, the glass particles used in the present invention may have a diameter of from 50 $\mu$m up to 2000 $\mu$m. More conveniently, however, the average diameter of the particles will be 1000 $\mu$m or less, usually 500 $\mu$m or less. Good results have been obtained with particles having an average diameter of 300 to 200 $\mu$m or less, for example 150 $\mu$m or less.

Particles having smaller diameters, e.g. 100 $\mu$m or less, particularly of approximately 50 $\mu$m, or even less, are of especial interest.

One advantage of the present invention is that it is possible to form glass particles having such small diameters (e.g. 50–100 $\mu$m). Where such small particles are used that problems associated with injection are reduced. Additionally, once the particles have been located in the site of interest, the outside surfaces of the particles becomes tacky as the particles begin to dissolve into body fluids so that the particles become associated in situ in a sticky cohesive mass.

Such particle association greatly reduces the rate of particle migration and the health risks associated therewith. No such association has been observed with the prior art silicone, PTFE or collagen beads.

A carrier medium is generally used to assist injection of the particles. The carrier medium is typically glycerol, but other conventional carrier mediums (e.g. corn oil, sesame oil, sunflower oil or olibas oil) may also be used. A surfactant and/or suspending agent may also be included in the composition. Typical surfactants include, for example, benzyl benzoate, ethyl oleate and benzyl alcohol. Typical suspending agents include, for example, carboxymethylcellulose and alginate.

In a further aspect the present invention provides a method of augmenting an area of soft tissue in a body (e.g. thickening a wall of a body organ), said method comprising injecting a composition into the soft tissue (e.g. the submucosa of said wall), said composition comprising particles of a biodegradable glass.

Thus, the present invention provides a method of combatting vesicoureteric reflux by injecting a composition of the present invention into the bladder submucosa close to the ureteral orifice such that urine is substantially unable to pass up the ureter upon contractor of the bladder.

Likewise, if the composition of the present invention is injected into the submucosa in the vicinity of the urethral sphincter, stress urinary incontinence may be overcome due to the "bulking" effect of the injected particles.

The present invention may be used at other body areas where soft tissue augmentation has a beneficial effect. Examples include injection around the anal passage, in order to reduce blood flow at the site and hence combat development of haemorrhoids (piles). Likewise soft tissue augmentation may be beneficial to temporarily correct an "incompetent" cervix which would prevent sustainment of a pregnancy. The soft tissue augmentation of the present invention may further be used to build up portions of the body damaged by accident or surgery, allowing healing to take place. Particular mention may be made of reshaping the facial area of a patient. From the above examples it is clear that the composition of the present invention may be used not only to treat existing conditions but also for prophylactic and cosmetic purposes.

Generally the glass will be a controlled release glass (CRG). CRGs sare vitreous inorganic polymers which dissolve over a pre-programmed period leaving virtually no residue. The components of manufacture are all present as natural body constituents hence CRCs show little or no cytotoxicity and exhibit a minimal tissue reaction.

The use of glasses which can dissolve in water and body fluid are well-known. These glasses are formed from phosphorus pentoxide and may be modified to dissolve over a period of months or years, as required. To date, such glasses have been used, in medicine, for the controlled release of a number of agents, for example, drugs, hormones and trace elements.

It is know that certain glasses, in which the usual glass former, silicon dioxide, of traditional glasses is replaced with phosphorus pentoxide as the glass former, are soluble in water and body fluids. The rate of dissolution is controlled largely by the addition of glass modifiers such as calcium and magnesium oxide. In simple terms, the greater the concentration of the modifier the slower the rate of dissolution. The rates of dissolution which can be imparted to the glasses may range from minutes to months or even to several years. It is known to include in such compositions quantities of trace elements such as copper, cobalt and selenium which will released from the glass as it slowly dissolves over the selected period of time.

The use of water-soluble glasses has been described for a variety of purposes in the literature. For example, UK Patent Specifications Nos 1,565,906, 2,079,152, 2,077,585 and 2,146,531 describe the gradual dissolution of the glasses as providing a means of controlled release of drugs, hormones, fungicides, insecticides, spermicides and other agents with which the glasses have been impregnated. The glasses are used, for example, in the form of an implant or bolus.

UK Patent Specification No 2,030,559 describes the use of selenium impregnated water-soluble glass for providing controlled release of the selenium as a trace element into cattle and sheep, the glass being applied as a subcutaneous insert. UK Patent Specification No 2,037,735 also describes a subcutaneous implant of water-soluble glass, and in this case the glass is impregnated with copper; minor quantities of trace elements such as boron, arsenic, iodine, manganese, chromium, silver, gold and gallium may also be included.

Water-soluble glass has also been proposed for use in prosthetics, for example in UK Patent Specification No 2,099,702, and for use in anticorrosive paints, as described in UK Patent Specification No 2,062,612. Further the literature provides for the use of such glasses in the controlled release of ferrous and ferric ions into the human or animal body by ingestion or implantation of the glass (UK Patent Specification No 2,081,703), and for the use of glasses in the controlled release of ions such as lithium, sodium, potassium, caesium, rubidium, polyphosphate, calcium and aluminium to patients by inclusion of the glass in a drip feed line (UK Patent Specification No 2,057,420).

Optionally he water-soluble glass may be a silver containing water-soluble glass. Advantageously the silver content my be introduced into the glass composition in the form of silver orthophosphate.

Suitable glasses include, for example, the ARGLAES™ glass of Giltech Limited.

The glass may be adapted by the use of glass modifiers to give a sustained release of silver ions over a set period.

In one embodiment the water-soluble glass comprises an alkali metal oxide $M_2O$, an alkaline earth oxide MO, phosphorus pentoxide $P_2O_5$ and silver oxide ($Ag_2O$) or silver orthophosphate ($Ag_3PO_4$).

Most preferably, said glass contains not more than 40 male % $M_2O$ or MO, not less than 10 mole % $M_2O$ or MO, and not more than 50 mole % nor less than 38 mole % phosphorus pentoxide, optionally with the inclusion of 0.05 to 5.0 mole % silver oxide or orthophosphate.

Said alkali metal oxide may be sodium oxide ($Na_2O$), potassium ($k_2O$) or a mixture thereof; and said alkaline earth oxide may be calcium oxide (CaO), magnesium oxide (MgO), zinc oxide (ZnO) or a mixture thereof.

The glass may also contain less than 5 mole % silicon dioxide ($SiO_2$), boric oxide ($B_2O_3$), sulphate ion ($SO_4^{2-}$), a halide ion, copper oxide (CuO) or a mixture thereof.

Typically the soluble glasses used in this invention comprise phosphorus pentoxide ($P_2O_5$) as the principal glass-former, together with any one or more glass-modifying non-toxic materials such as sodium oxide ($Na_2O$), potassium oxide ($K_2O$), magnesium oxide (MgO), zin oxide (ZnO) and calcium oxide (CaO). The rate at which the silver-release glass dissolves in fluids is determined by the glass composition, generally by the ratio of glass-modifier to glass-former and by the relative proportions of the glass-modifiers in the glass. By suitable adjustment of the glass composition, the dissolution rates in water at 38° C. ranging from substantially zero to 25 $mg/cm^2/hour$ or more can be designed. However, the most desirable dissolution rate R of the glass is between 0.01 and 2.0 $mg/cm^2/hour$. The water-soluble glass is preferably a phosphate glass, and the silver may advantageously be introduced during manufacture as silver orthophosphate ($Ag_3PO_4$). The content of silver and other constituents in the glass can vary in accordance with conditions of use and desired rates of release, the content of silver generally being up to 5 mole %. While we are following convention in describing the composition of the glass in terms of the mole % of oxides, of halides and of sulphate ions, this is not intended to imply that such chemical species are present in the glass nor that they are used for the batch for the preparation of the glass.

The glass may be formed by a number of methods. It may simply be cast by conventional or centrifugal procedures, or it may be prepared via one or more stages of rod, fibre or tube drawing. Other preparation techniques include foamed glass. Following glass formation it will be comminuted into finely divided form.

Optionally, the composition of the present invention may contain an active ingredient. The term "active ingredient" is used herein to refer to any agent which affects the metabolism or any metabolic or cellular process of the patient (including growth factors and living cells), promotes healing, combats infection, hypergranulation or inflammation. Antibiotics and other anti-bacterial agents, steroids, painkillers etc are all suitable. Optionally, the active ingredient may be in delayed-release or controlled-release form.

The invention will now be further described with reference to the following, non-limiting, examples and Figures in which:

FIG. 1 H and E staining of 1240596-1 glass granule intramucular (six months). Magnification×125.

Figure 2:

FIG. 2 H and E staining of 1240596-2 glass granule intramuscular (six months). Magnification×125.

Figure 3:
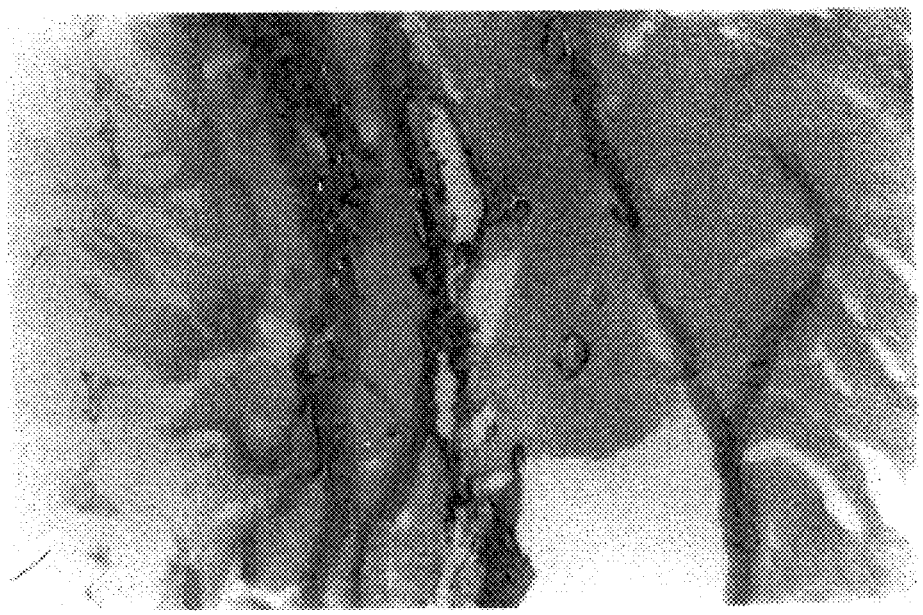

FIG. 3 H and E staining of 1240596-3 glass granule intramuscular (six months). Magnification×125.

Figure 4:
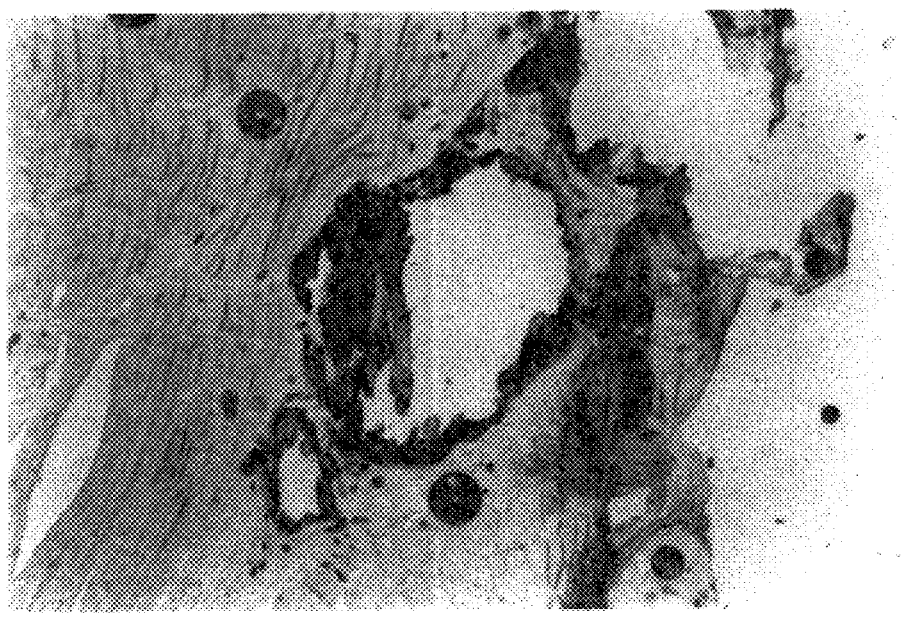

FIG. 4 Neutrophil staining of muscle section containing implant 1240596-1. Magnification×125 (black circles are air bubbles).

Figure 5:
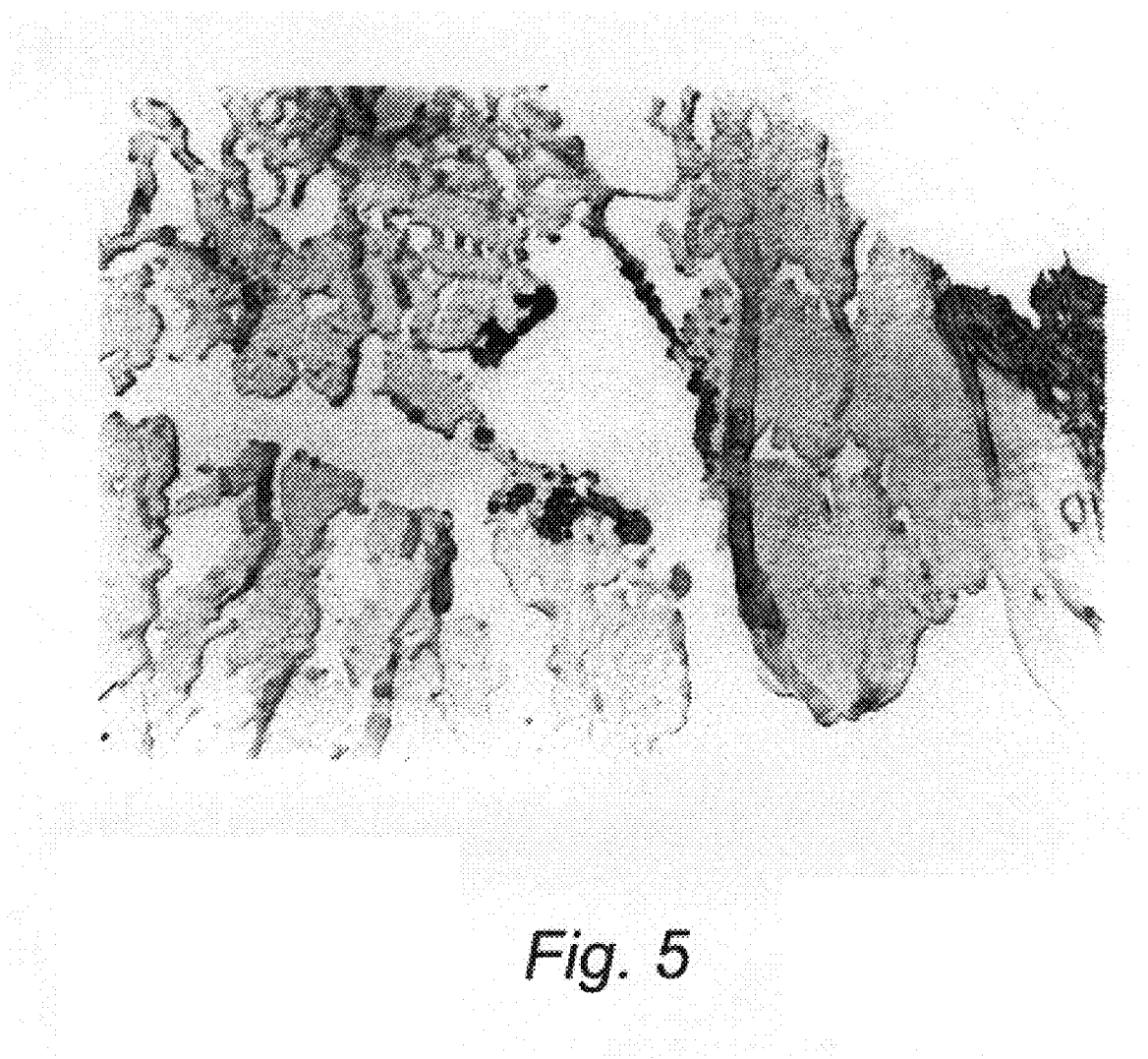

FIG. 5 Macrophage staining of muscle section containing implant 1240596-2. Magnification×125.

EXAMPLE 1

The CRGs will be implanted in vivo to assist in the evaluation of attenuation of the solution rate of the glass and to observe the acute tissue reaction at the submucosal implant site.

Materials

Two CRG compositions with slow solution rates (to be decided) will be prepared as rough granules 200–300 μm in diameter. The granules will be suspended in glycerine BP, 8.5 ml glycerine to 10 g CRG. The suspensions will be packaged 2.5 ml in syringes. The syringes will be individually sealed in foil polyester/polyester pouches and sterilized by γ irradiation.

Method

The anterior bladder wall of the anaesthetised model (rabbit) is exposed and a small volume (0.5 ml) of CRG implant is injected into the submucosa on the left and right anterior bladder wall midway between the ureters and the neck of the bladder. The implant should create a small visible mound at the implant site. It is suggested that the CRGS used at the left and right sites be of different solution rates, or that one of the sites contains an existing "control" implant material for comparison (eg RACROPLASTIQUE (Trade Mark) of Uroplasty, Inc ten animals would be required.

Evaluation

By placing the implants in the anterior bladder wall, it should be possible to look at the implant on a weekly basis using ultrasound. In addition, two animals would be sacrificed at two weeks, one month, six months and twelve months.

The ultrasound examinations should look at the implant material and any migration from the implant site should be reported. Acute fibrous capsule formation should be recorded. It may be possible to differentiate the CRG and its dissolution over the more prolonged terms.

On sacrifice, tissue reactions and acute inflammation should be recorded. Fibrous capsule development should be noted and presence of CRG (and glycerol in early stages) quantified for each implant site. Samples of surrounding tissues should be removed for histological examinations.

Results and Interpretations

An initial inflammatory response is anticipated at the implant site. It is hoped that a collagen capsule will form around the CRG granules. This capsule is expected to reduce the solution rate of the glass. It will be helpful to measure the attenuation of solution rate due to reduced fluid transport within the capsule. By one month surrounding tissue inflammations should have subsided and histology should show normal cell response. There should be no migration of the CRG implant beads and the glycerol should be completely removed within the first two weeks.

In each sacrifice group there should be at least one "control" implant. The tissue response of the control should be compared with the CRG implant results.

EXAMPLE 2

Materials ad Methods

Controlled release glasses (CRGS) were formulated as follows:

| | mole % concentrations | | |
|---|---|---|---|
| | $Na_2O$ | $CaO$ | $P_2O_5$ |
| I240596-1 | 5 | 48 | 47 |
| I240596-2 | 15 | 38 | 47 |
| I240596-3 | 25 | 28 | 47 |

A granular diameter range of 53–1000 μm was used for all CRGs.

0.1 g samples of the CRGs listed above were sterilised by dry heat (190° C. for 3 hours) before implantation into black and white hooded Lister rats (Liverpool strain). Two samples were implanted into each animal. Three animals were employed at a time period of six months. The implants were placed bilaterally into a pocket created in the dorsa-lumbar muscle region of the animal. At the six month time of explantation, the implant and surrounding tissue was removed from the sacrificed animal and frozen immediately. The frozen sample was sectioned at 7 μm in a microtome cryostat. Analysis of the implant/tissue site was performed by staining the sample sections for various cytokines. A haematoxolin and eosin (H and E) stain was carried out on each of the six retrieved samples, as well as neutrophil and macrophage staining. Immunohistochemical staining for ED1, ED2, CD4, CD8, Interleukin-1β (IL-1β), IL-2, Major Histocompatibility Complex (MHC) class II, α-β and Anti-β antigens have been completed. These stains allow the tissue response to the implant presence to be evaluated in the following manner:

| | |
|---|---|
| H and E | Stains all viable cells and allows the tissue type and fibrous capsule to be easily identified by the characteristic structure shape of each tissue. |
| ED1 | Recognizes rat macrophages, monocytes and dendritic cells. Granulocytes are negative. The recognized antigen is predominantly located intracellularly, although some membrane expression occurs. |
| ED2 | Recognizes a membrane antigen on resident rat macrophages; monocytes, dendritic cells and granulocytes are negative. No other cell types but macrophages are positive for ED2, and it discriminates between thymic cortical (ED2+) and medullary macrophages (ED2−). |
| CD4 | Expressed on most thymocytes and approximately two thirds of peripheral blood T cells. In humans and rats, CD4 is expressed on monocytes and macrophages. CD4 is an accessory molecule in the recognition of foreign antigens in association with MHC class II antigens by T cells. |

-continued

| | |
|---|---|
| CD8 | Expressed on most thymocytes and approximately one third of peripheral blood T cells, which constitute the CD4 negative cells. CD8α is in all natural killer (NK) cells in the rat. |
| IL-1β | Expressed by B cells, macrophages and monocytes and its mRNA is present in a number of cells including T cells. In addition to activating T and B lymphocytes, interleukin-1 (IL-1) induces several haematological and metabolic changes typical of host response to infection and injury. IL-1 is an endogenous pyrogen, producing fever by its ability to increase hypothalamic prostoglandin. IL-1 also induces the release of several lymphokines, interferons and colony stimulating factors. With the exception of skin keratinocytes, some epithelial cells and certain cells in the central nervous system, mRNA coding for IL-1 is not observed in health in most other cells. |
| IL-2 | More descriptively, T cell growth factor, has promise as an immune stimulant and an anti-tumour agent. IL-2 recognizes activated rat T cells but not resting lymphocytes |
| MHC Class II | Expressed by dendritic cells, B cells, monocytes, macrophages and some epithelial cells. Expression is increased by interferon α which also induces expression on fibroblasts, epithelial and endothelial cells. |
| α-β | Detects an α-β T cell receptor. |
| Anti-β | Directed at leucocytes. Also labels B cells among thoracic duct lymphocytes with little labelling in bone marrow and none on thymocytes. Acts as an isotope control. |

Results and Discussion

The photographs in FIGS. 1–3 show H and R staining of the I2405961-3 implants respectively. As can be seen in these Figures, fibrous capsules have fonred around each glass granule. Glass I240596-1 has the slowest solution rate as tested in-vitro, and this can be seen in FIG. 1 also, as the sizes of the remaining glass granules in the rat muscle after six months are considerably larger compared to the other two glass composition which both have faster solution rates (I240596-3 has the fastest solution rate in-vitro). The surrounding muscle tissue to the implant appears healthy. FIGS. 4 and 5 show photographs of neutrophil staining of implant section I240596-1 and macrophage staining of I240596-2 respectively. These photographs are typical of all the slides viewed, as all six sections contained insignificant neutrophil and macrophage presence in the tissue. In the photograph of the neutrophil stained section, it can be seen that there are several mast cells near the implant site and throughout the tissue. This is expected in normal, healthy muscle tissue. The lack of macrophages and neutrophils indicates a lack of inflammatory response to the implant, showing that after a six month period, the glass granules appear to be accepted in-vivo.

The cytokine staining of the above antigens were all negative, correlating with the absence of neutrophils and macrophages in the tissue sections. Cytokines are regulatory peptides that can be produced by virtually every nucleated cell in the body, such as lymphocytes and monocytes. Cytokines are generally not constitutively produced, but are generated in emergencies to contend with challenges to the integrity of the host. Cytokines achieve these ends by mobilizing and activating a wide variety of target cells to grow, differentiate and perform their functions. This means that cytokines are key mediators of immunity and inflammation. The insignificant staining of the above indicates the acceptance of the glass implant into the body and shows that the glass presence is not inducing any inflammatory reaction in-vivo.

Conclusion

All the sections stained and viewed after the six month period showed healthy, normal muscle tissue containing a fibrous capsule coated glass granule. Staining of various cytokines gave a negative result, indicating the absence of inflammatory responses of the muscle tissue with the glass presence after six months.

EXAMPLE 3

Soft Tissue Response to Glycerol Suspended Controlled Release Glass Particulates This example investigated the soft tissue response of glasses with a range of particulate sizes of different dissolution rates, transported in a glycerol carrier.

Materials and Methods

The CRG was tested in particulate form of three different compositions and two different particulate sizes: x (200–300 μm, 0.02 mg/cm$^2$/hr solution rate), Y (200–300 μm 0.12 mg/cm$^2$/hr solution rate) and Z (<53 μm, 0.34 mg/cm$^2$/hr solution rate), all suspended in glycerol. A control sample of glycerol only was also included in the experiment and was labelled sample W. Samples weighing 0.1 grams of each of the CRG's in glycerol and glycerol only were sterilised by gamma irradiation before implantation intramuscularly into Wistar rats. Two samples were implanted into each animal. Four animals at each time period of 2 days, 4 weeks, 9 weeks and 6 months were employed. The implants were placed bilaterally into a pocket created in the dorso-lumbar muscle of the animal. At the time of explantion, the implant and surrounding tissue was removed from the sacrificed animal and snap frozen. A microtome cryostat was used to cut 7 μm thick serial sections. Analysis of the implant/tissue site was performed by specific staining the sample sections for various cell types. Neutrophils and macrophages were stained using enzyme histochemistry, ED1 (monocytes and immunature macrophages), ED2 (mature tissue macrophages), CD4 (helper/inducer T-lymphocytes and macrophages), CD8 (suppressor/cytotoxic T-lymphocytes), interleukin-1β, IL-2 (activated T-lymphocytes), Major Histocompatibility Complex (MHC) class II (activated macrophages and activated B-lymphocytes), α-β (T-lymphocyte) and CD45RA (B lymphocytes) antibodies have been used to immunohistochemically stain each sample.

Results ant Discussion

Positive staining for neutrophils was observed after 2 day implantation with all of the materials. The neutrophils present were found in localised clusters near the implant site. However, neutrophils were not seen in the tissue sections of each of the implanted glasses or glycerol in the remaining time periods. Mast cells were present in all tissue samples, but it was noticed that an increased number of these cells were present in clusters near the implanted glass in sections containing glass X at 6 months, glass Y at 2 days and 6 months and glass Z at 4 weeks and 6 months. Enzyme staining and immunohistochemical staining both confirmed the presence of macrophages in all sections at all time periods except glass X at 6 months. The neutrophil presence at 2 days in all sections suggest an acute inflammatory response. The absence of these cells however in the remaining time periods indicate that this acute inflammation is quickly resolved. However, the presence of macrophages in all samples at all time periods except X at 6 months indicate an ongoing chronic inflammatory response to the presence of the implanted material. With glass X however, this chronic inflammatory response appears to have been resolved at 6 months. With one material, glass Z, tissues necrosis in association with the glass at 4 weeks and 9 weeks has been observed. This study demonstrates that particulate, degrading glass is stimulating an inflammatory response in soft tissue of time periods up to 6 months. It should be noted that very small particulate fast degrading glass is leading to tissue necrosis and should be further considered for these applications. However, larger particulate, slower degrading materials are demonstrating effective potential for stress incontinence applications.

EXAMPLE 3

Inflammatory Response to Controlled Release Glass

Samples of a range of compositions of Controlled Release Glasses (CRGS) in granular form were analysed for the soft tissue response to determine their biocompatibility.

Materials and Methods

The CRG was tested in granular form (53–1000 $\mu$m) of three different compositions: A (high in CaO, slow solution rate), B (medium solution rate) and C (low in CaO, fastest solution rate). Samples weighing 0.1 grams of each of the CRG's were sterilized by dry heat (3hrs, 190° C.) before implantation into black and white hooded Lister rats. Two samples were implanted into each animal. Three animals were employed at each time period of 2 days, 1 week, 4 weeks, 8 weeks and 6 months. The implants were placed bilaterally into a pocket created in the dorso-lumbar muscle of the animal. At the time of explantion, the implant and surrounding tissue was removed from the sacrificed animal and snap frozen. The frozen sample was sectioned at 7 $\mu$m thickness in a microtome cryostat. Analysis of the implant/tissue site was performed by using different staining techniques Immunohistochemical staining using ED1 (monocytes and immature macrophages), ED2 (mature tissue macrophages), CD4 (helper/inducer T-lymphocytes and macrophages), CD8 (suppresser/cytotoxic T-lymphocytes), interleukin-1$\beta$, IL-2 (activated T-lymphocytes), Major Histocompatibility Complex (MHC) class II (activated macrophages and activated T-lymphocytes), $\alpha$-$\beta$ (T-lymphocytes) and CD45RA ($\beta$-lymphocytes) antibodies have been performed. A haematoxylin and eosin (H and E) stain was carried out on each of the retrieved samples. Neutrophil and macrophage enzyme staining was also performed.

Results and Discussion

The tissue response to the range of CRG's can clearly be demonstrated as being different and dependant on the materials, involving neutrophils, macrophages and mast cells and not involving T or B lymphocytes.

Localised clusters of neutrophils were observed after 2 days implantation of each of the CRG's A, B and C. However, neutrophils were not seen in the tissue sections of each implanted glass in each of the remaining time periods.

Mast cells were scattered throughout all tissue sections as expected, but it was noticed that an increased number of these cells were present in clusters near the implant in sections containing CRG A at 9 weeks and 6 months, and in CRG C at 2 days, 9 weeks and 6 months.

The most predominant cell type in all sections was the macrophage confirmed by both enzyme staining and immunohistochermistry. Macrophages were observed in all of the sections for all of the time periods and were positive for ED1, ED2 and MHCII antibodies. The presence of neutrophils at 2 days in all three glass compositions indicate that an acute inflammatory response has occurred. The absence of the neutrophils at all subsequent time periods suggest that the acute inflammatory phase had resolved. However, the observation of macrophages throughout all time periods up to and including 6 months indicates continued stimulus by the materials of a chronic inflammatory phase response.

What is claimed is:

1. A composition suitable for implantation in soft tissue, said composition comprising particles of biodegradable phosphate glass in a carrier medium.

2. A composition as claimed in claim 1 wherein the glass particles are irregularly shaped.

3. A composition as claimed in claim 1 wherein said particles have a diameter of 1000 $\mu$m or less.

4. A composition as claimed in claim 1 wherein said particles have a diameter of 300 $\mu$m or less.

5. A composition as claimed in claim 1 wherein said particles have a diameter of 50 $\mu$m to 100 $\mu$m.

6. A composition as claimed in claim 1 wherein said carrier medium is glycerol.

7. A composition as claimed in claim 1 wherein said carrier medium includes a surfactant and/or a suspending agent.

8. A composition as claimed in claim 1 comprising glass particles formed from a controlled release glass.

9. A composition as claimed in claim 1 comprising glass particles formed from a water soluble glass.

10. A composition as claimed in claim 1 comprising glass particles formed from a silver containing glass.

11. A method for augmentation of soft tissue comprising implanting the composition comprising particles of biodegradable phosphate glass in a carrier of claim 1 in soft tissue.

12. The method of claim 11 wherein said soft tissue is the submucosa of the urethral sphincter.

13. A method of augmenting an area of soft tissue in a body, said method comprising injecting a composition as claimed in claim 1 into the soft tissue.

14. A method as claimed in claim 13 which is used augment soft tissue for cosmetic purposes.

15. A method as claimed in claim 13 wherein said soft tissue is the submucosa of a wall of a body organ.

16. A method of combatting vesicoureteric reflux by injecting a composition as claimed in claim 1 into the bladder submucosa close to the urethral orifice such that urine is unable to pass up the ureter upon contraction of the bladder.

* * * * *

UNITED STATES PATENT AND TRADEMARK OFFICE
CERTIFICATE OF CORRECTION

PATENT NO. : 6,447,805 B1
DATED : September 10, 2002
INVENTOR(S) : David Michael Healy It is certified that error appears in the above-identified patent and that said Letters Patent is hereby corrected as shown below:

Title page,
Item [57], ABSTRACT, replace:

"A composition suitable for implantation in soft tissue (for example at or around a body orifice) in order to augment the volume of soft tissue is produced."
with -- A composition suitable for implantation in soft tissue (for example at or around a body orifice) in order to augment the volume of soft tissue produced. --

Column 10,
Lines 49-50, replace:

"14. A method as claimed in claim 13 which is used augment soft tissue for cosmetic purposes."

with  -- 14. A method as claimed in claim 13 which is used to augment soft tissue for cosmetic purposes. --

Signed and Sealed this

Twenty-fifth Day of February, 2003

JAMES E. ROGAN
*Director of the United States Patent and Trademark Office*